United States Patent [19]

Allan et al.

[11] 3,936,496

[45] Feb. 3, 1976

[54] ORGANIC COMPOUNDS

[75] Inventors: Zdenek Allan, Allschwil; August Schweizer, Muttenz, both of Switzerland

[73] Assignee: Sandoz Ltd., (Sandoz AG), Basel, Switzerland

[22] Filed: Dec. 13, 1972

[21] Appl. No.: 314,675

[30] Foreign Application Priority Data

Dec. 15, 1971 Switzerland.................... 18353/71
Jan. 31, 1972 Switzerland...................... 1379/72
Feb. 17, 1972 Switzerland...................... 2297/72

[52] U.S. Cl................................ 260/510; 260/180
[51] Int. Cl.²...................................... C07C 143/56
[58] Field of Search............................ 260/508, 510

[56] References Cited

UNITED STATES PATENTS 2,765,301  10/1956  Cashion .............................. 260/508

FOREIGN PATENTS OR APPLICATIONS 204,212    8/1907  Germany ............................ 260/508
1,486,851  6/1967  France ................................ 260/508
100,613    7/1897  Germany ............................ 260/508

OTHER PUBLICATIONS

Roberts et al., "Basic Principles of Organic Chem.," pp. 869–871, (1965).

Sandler et al., Organic Functional Preparations, Vol. 12, pp. 347–348, (1968).
Bloink et al., Journal Chemical Society, pp. 950–954, (1950).
Martynoff, Bull. Soc. Chim., France, (1951), 214.
Martynoff, Compt. Rend., 223, 747, (1946).
Baeyer, Ber., 1, 1638, (1874).
Bates, "The Synthesis of Benzene Derivatives," pp. 62–63, 108–111, D. Van Nostrand Co., N.Y., 1926.
Roberts et al., "Basic Principles of Organic Chemistry," W. A. Benjamin, Inc., New York, pp. 869–871, (1965).

*Primary Examiner*—James O. Thomas, Jr.
*Assistant Examiner*—Nicky Chan
*Attorney, Agent, or Firm*—Gerald D. Sharkin; Richard E. Vila; Thomas C. Doyle

[57] ABSTRACT

The invention concerns a novel process for the production of benzidine compounds having at least one nuclear sulphonic acid group, comprising reacting a nitro- or nitroso-benzene with an aniline or mono-N-alkyl aniline, reducing the reaction product to a hydrazo compound and rearranging this to the benzidine compound.

9 Claims, No Drawings

ORGANIC COMPOUNDS

The present invention relates to a process for the production of benzidine derivatives.

The invention provides a process for the production of compounds of Formula I,

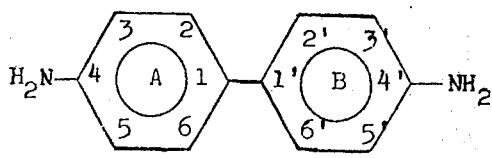

in which in rings A and B at least one of the positions 2,3,5,6,2',3',5' and 6' is substituted by a sulphonic acid group and the rings A and B are otherwise unsubstituted or substituted by halogen of atomic number from 9 to 53 and/or by alkyl or alkoxy of 1 to 6 carbon atoms, which comprises reacting a compound of formula II,

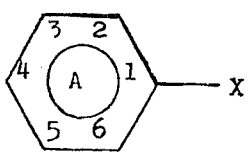

in which X signifies $NO_2$ or $-NO$, and the ring A is defined as above, the position 4 being unsubstituted, with a compound of formula III,

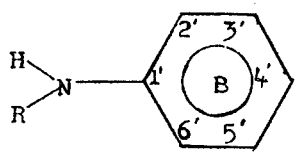

in which

R signifies hydrogen or an alkyl radical capable of being split off in the reaction with the compound of formula II, and ring B is as defined above, the position 4' being unsubstituted, with the provisos that if R signifies an alkyl radical, then X signifies $-NO_2$ and if X signifies $-NO$, then R signifies hydrogen, and reducing the reaction product to a hydrazo compound of formula IV,

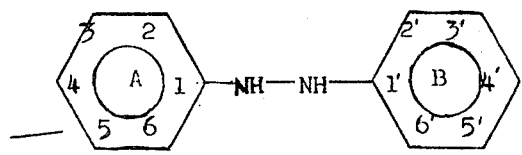

in which rings A and B are as defined above, the positions 4 and 4' being unsubstituted, and rearranging the compound of formula IV to produce the compound of formula I.

When rings A and/or B are substituted by halogen this is preferably chlorine; preferred alkyl or alkoxy substituents are of 1 or 2 carbon atoms, for example methyl, ethyl, methoxy or ethoxy.

If X in formula II signifies $-NO_2$, R in formula III signifies hydrogen or, preferably, an optionally substituted alkyl radical, which latter radical may be any radical which is split off in the reaction to give rise to an oxidation product of R. Preferably R signifies methyl, ethyl or $\beta$-hydroxyethyl.

The process of this invention is specially suitable for the production of asymmetrical compounds of formula (I), in particular of compounds which contain only one sulphonic acid group or in which the rings A and B each bears one sulphonic acid group. The process of the present invention is conveniently used for the production of compounds of formula Ia or Ib,

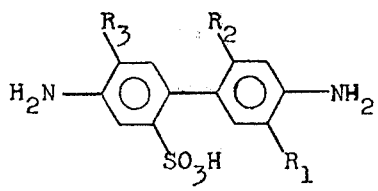

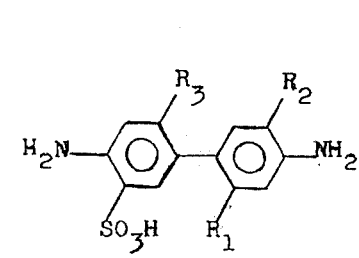

in which $R_1$ and $R_3$ each independently signifies hydrogen, halogen or alkyl or alkoxy containing 1 to 6 carbon atoms and $R_2$ signifies hydrogen, halogen, alkyl or alkoxy containing 1 to 6 carbon atoms or the sulphonic acid group.

On the reaction of a compound of formula II in which X signifies $-NO$ with a primary amine of formula III an azo compound of formula VII,

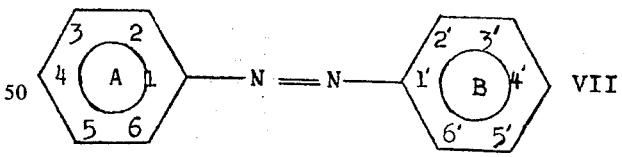

in which rings A and B are as defined above, is formed. The reaction may suitably be carried out in basic (pH 8–15) or acid (pH 6–2) medium, at temperatures from about room temperature to the boiling point of the reaction mixture, preferably between 50° and 80°C. If an acid, for example an acetic acid, medium is employed, it is preferred to add a catalyst, e.g., a tertiary amine such as pyridine, lutidine or quinoline.

The reaction of a compound of formula II in which X signifies $-NO_2$ with a compound of formula III in which R signifies hydrogen, yields an azo compound of formula VII or, may possibly, under particular conditions, yield an analogous azoxy compound. The reaction is conveniently carried out in a strongly alkaline medium, for example at pH of at least 12, preferably between 14 and 15. The reaction is preferably carried out at elevated temperature, advantageously at least 50°C, preferably from 70°C to the boiling point of the reaction mixture, or at higher temperatures under pressure, if necessary with the addition of an oxygen acceptor, for example glucose, molasses or glycerine. The reaction of a compound of formula II in which X signifies $-NO_2$ with a compound of formula III in which R is different from hydrogen yields azo compounds of formula VII; the reaction of the nitro compound with the secondary amine is suitably carried out under the same conditions as the reaction with the primary amine described above but the addition of an oxygen acceptor is not necessary.

It may be noted that the reaction of compounds of formulae II and III in alkaline medium results in the reaction product being formed in alkali salt form.

Subsequent reduction to the hydrazo compounds of formula IV may be carried out by any of the conventional methods in which reduction does not proceed beyond the hydrazo stage, for example with a base metal or an alloy of base metals, for example zinc or silicon or sodium amalgam, in an aqueous, strongly alkaline medium, for example in the presence of sodium or potassium hydroxide, preferably in the absence of air and preferably with heating, for example at temperatures from 70°C to the boiling temperature of the reaction mixture, especially between 80° and 90°C. Reduction may also be accomplished electrolytically in alkaline medium. Further suitable reduction methods are described, for example, in Houben-Weyl, Methoden der Organischen Chemie, 4th impression (1967), Vol. X/2, pp. 705–724.

The rearrangement of the hydrazo compounds of formula IV to the benzidine compounds of formula I may be carried out in conventional manner, for example in strongly acid medium (pH 1.5 – 0), for example using hydrochloric acid, and suitably at temperatures from 10° to 50°C.

Reduction may also be carried out with simultaneous rearrangement by the use of tin dichloride as reducing agent in a concentrated hydrochloric acid medium (pH 1.5 – 0) and at temperatures from 0° to 30°C. It is preferred to de-tin the reaction mixture by one of the known methods, for example by electrolysis, before the final product is isolated. It is not known for certain whether the hydrazo intermediate of formula IV is formed transitorily in this simultaneous process, but it is to be understood to fall under the process of this invention.

The newly formed compounds, if desired after neutralization of the excess acid, may be isolated by the normal methods and if necessary purified.

The compounds of formula I may be used as intermediates for the production of anionic dyes in well known manner. For example, 4,4'-diamino-1,1'-diphenyl-3-sulphonic acid serves as an intermediate for the production of anthraquinone and azo dyes of anionic character, as described, for example, in French Pat. Nos. 1,211,502, 1,486,851 and 1,540,735.

In the following Examples the parts and percentages, unless otherwise stated, are by weight and the temperatures in degrees centrigrade. The parts by weight relate to the parts by volume as grams to millilitres.

EXAMPLE 1

Aqueous sodium hydroxide solution containing 8 parts of sodium hydroxide is made up to 70 parts by volume with water and 20.3 parts of 3-nitrobenzenesulphonic acid in the form of the sodium salt and 10.7 parts of N-methyl-aniline are added. The solution is reacted at the boiling temperature for 20 hours with reflux. After distillation of the unreacted N-methylaniline with water vapour, 8 parts of sodium chloride are added and the solution allowed to cool to 20°. The crystalline precipitate is filtered with suction and dried at 100°. Chromatographic analysis of the sodium salt of azobenzene-3-sulphonic acid thus formed shows it to be virtually pure. It is obtained as a red-brown cystalline powder which dissolves in water with a yellow colour. On heating it carbonizes slowly without melting.

26.2 Parts of this azobenzene-3- sulphonic acid sodium salt are dissolved in 280 parts of water at 60° and the solution cooled to room temperature, on which the azo compound settles out as fine crystals.

28 parts of tin (II)) chloride dihydrate are entered into 60 parts by volume of 36.5% hydrochloric acid and stirred for about 6 hours at room temperature until completely dissolved. The solution is allowed to flow in about 30 minutes into the dye suspension. Ice is added from time to time to keep the reaction temperature below 30°.The hydrazo compound is formed with decolouration and is simultaneously rearranged to 4',-4'-diamino-1,1'-diphenyl-2-sulphonic acid. The resulting solution is diluted with 150 parts of water and clarified by filtration. It is then de-tinned. Copper is used as anode and a graphite rod standing in a diaphragm filled with hydrochloric acid is used as cathode. Electrolytic de-tinning is carried out at room temperature. After complete separation of the tin the solution is again clarified by filtration. Then its pH is adjusted to 4.2 by the addition of aqueous sodium hydroxide solution, on which the 4,4'-diamino-1,1'-diphenyl-2-sulphonic acid is completely precipitated. It is filtered and dried at 100°. The dry powder is of pale grey colour and is poorly soluble in water, but soluble in alkalis and dilute mineral acids.

EXAMPLE 2

An amount of the sodium salt of 2-nitrobenzenesulphonic acid equivalent to 20.3 parts of the free sulphonic acid and 9.3 parts of aniline in 26 parts of 30% sodium hydroxide solution are held at the boiling temperature for 30 minutes with stirring and reflux, and subsequently diluted with 50 parts of water. Firstly unreacted aniline is distilled with water vapour, and then, after neutralization with hydrochloric acid, the 2-nitro-1-hydroxybenzene formed as by-product. Filtering earth is added, then the remaining solution is filtered while hot and the product precipitated from the filtrate with sodium chloride. It is isolated by filtration with suction and dried. Chromatography of the sodium salt of azobenzene-2-sulphonic acid thus formed shows that it is virtually homogeneous. It is obtained as a crystalline powder which dissolves readily in water to give a yellow solution. On heating it carbonizes slowly without melting.

26.2 Parts of this sodium salt of azobenzene-2-sulphonic acid are dissolved in 300 parts of water at 60°. A concentrated aqueous solution of 18 parts of sodium hydroxide is added to adjust the solution to the strongly alkaline region. It is raised to 80° and in the absence of air 7.5 parts of zinc powder are added in portions in about 30 minutes. Stirring is continued for about 2 hours at 80°–89° until the reaction solution is decolourised. It is filtered free of the zinc sludge, cooled to 10° and run into 110 parts by volume of 30% hydrochloric acid. Ice is added as required to keep the temperature at 10° to 15°. To complete the rearrangement of the hydrazobenzene-2-sulphonic acid into the 4,4'-diamino-1,1'-diphenyl-3-sulphonic acid, stirring is continued for 10 hours and finally the temperature is increased to 40°. The pH is adjusted to 5.5 with concentrated aqueous sodium hydroxide solution, on which the 4,4'-diamino-1,1'-diphenyl-3-sulphonic acid is precipitated from the solution. It is filtered and dried at 100°.

EXAMPLE 3

40.6 Parts of 3-nitrobenzenesulphonic acid in the form of the sodium salt, 20 parts of aniline, 250 parts of water, 35 parts of 30% sodium hydroxide solution and 20 parts of glycerin (as oxygen acceptor) are reacted for about 48 hours at 90° with stirring and reflux condensation. The reaction solution gradually acquires an intense yellow colour. On completion of the reaction the excess aniline is distilled with water vapour. The remaining dye solution is set with sodium chloride and cooled, on which the sodium salt of azobenzene-3-sulphonic acid settles out as yellow crystals. It is filtered and dried.

Reduction of the azobenzene-3-sulphonic acid to the corresponding hydrazo compound and rearrangement to the 4,4'-diamino-1,,1'diphenyl-2-sulphonic acid can be carried out in accordance with the procedure described in Example 1 or 2.

EXAMPLE 4

17.3 Parts of 1-aminobenzene -3-sulphonic acid are dissolved in 35 parts of water and 100 parts of pyridine with heating, 70 parts of 100% acetic acid are slowly added and the solution adjusted to 80°. After the addition of 10.7 parts of nitrobenzene in small portions the reaction mixture is stirred for 2 hours at 80°.The solvent is distilled under reduced pressure. The residue is dissolved in water and 5.3 parts of sodium carbonate with heating, some filtering earth is added to the solution and it is then filtered while hot. On the addition of sodium chloride and cooling, the sodium salt of azobenzene-3-sulphonic acid settles out. It is filtered and dried.

Reduction of the azobenzene-3-sulphonic acid to the corresponding hydrazo compound and rearrangement to the 4,4'-diamino-1,1'-diphenyl-2-sulphonic acid can be carried out in analogy with the procedures given in Example 1 or 2.

In the table below further compounds of formula I are specified which can be produced in analogy with the procedures of Examples 1 to 4. They are distinguished in the table by the starting compounds of formulae II and III and by the structural formula of the resulting compound.

Table

| Example No. | Compound of formula II | Compound of formula III | Final product |
| --- | --- | --- | --- |
| 5 | 2-methyl-3-nitrobenzenesulphonic acid (HO₃S, NO₂, CH₃ substituents) | N-ethyl-4-methylaniline (C₂H₅NH–, CH₃) | 3,3'-dimethyl-4,4'-diamino-1,1'-diphenyl-x-sulphonic acid (H₂N–, CH₃ / CH₃, –NH₂, SO₃H) |
| 6 | 3-nitrobenzenesulphonic acid (HO₃S, NO₂) | N-(2-hydroxyethyl)-3-methoxyaniline (HOC₂H₄NH–, CH₃O) | 3'-methoxy-4,4'-diamino-1,1'-diphenyl-x-sulphonic acid (H₂N–, OCH₃, –NH₂, SO₃H) |
| 7 | 3-nitrobenzenesulphonic acid (HO₃S, NO₂) | 3-ethoxyaniline (H₂N–, C₂H₅O) | 3'-ethoxy-4,4'-diamino-1,1'-diphenyl-x-sulphonic acid (H₂N–, OC₂H₅, –NH₂, SO₃H) |
| 8 | 3-methoxy-5-nitrobenzenesulphonic acid (HO₃S, NO₂, OCH₃) | N-methyl-3-methoxyaniline (CH₃NH–, CH₃O) | 3,3'-dimethoxy-4,4'-diamino-1,1'-diphenyl-x-sulphonic acid (H₂N–, CH₃O / OCH₃, –NH₂, SO₃H) |
| 9 | 3-nitrobenzenesulphonic acid (HO₃S, NO₂) | 3-chloroaniline (H₂N–, Cl) | 3'-chloro-4,4'-diamino-1,1'-diphenyl-x-sulphonic acid (H₂N–, Cl, –NH₂, SO₃H) |
| 10 | 3-nitrobenzenesulphonic acid (HO₃S, NO₂) | 4-methyl-3-aminobenzenesulphonic acid (H₂N–, CH₃, SO₃H) | 3-methyl-4,4'-diamino-1,1'-diphenyl-2,2'-disulphonic acid (H₂N–, HO₃S / SO₃H, –NH₂, CH₃) |

Table-continued

| Example No. | Compound of formula II | Compound of formula III | Final product |
|---|---|---|---|
| 11 | | | |
| 12 | | | |

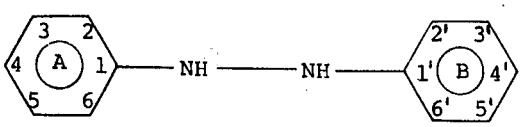

What we claim is:
1. A process for the production of compounds of formula I,

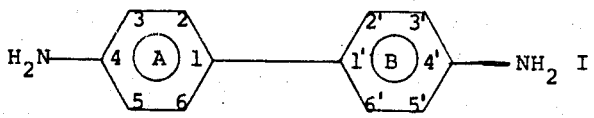

in which in ring A at least one of the positions 2, 3, 5 and 6 is substituted by a sulphonic acid group and the rings A and B are otherwise unsubstituted or substituted by halogen of atomic number from 9 to 53 and/or by alkyl or alkoxy of 1 to 6 carbon atoms, which comprises reacting a compound of formula II,

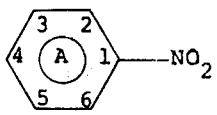

in which the ring A is defined as above, the position 4 being unsubstituted, with a compound of formula III,

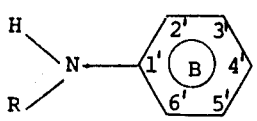

in which
R signifies methyl, ethyl or β-hydroxyethyl, and
ring B is as defined above, the position 4' being unsubstituted,
at a temperature of at least 50°C and a pH of at least 12, and reducing the resulting azo reaction product, under conditions whereby the reduction does not proceed beyond the hydrazo stage, to a hydrazo compound of formula IV,

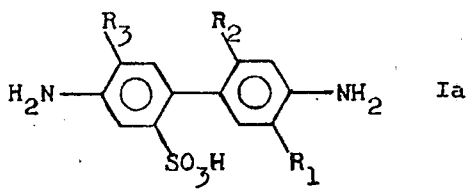

in which rings A and B are as defined above, the positions 4 and 4' being unsubstituted, and rearranging the compound of formula IV in a strongly acid medium to produce the compound of formula I.

2. A process according to claim 1 wherein the step of reducing the azo compound to the hydrazo compound is carried out in alkaline medium.

3. A process according to claim 2, in which the reduction of the reaction product of the compounds of formulae II and III is carried out using a base metal in an aqueous strongly alkaline medium.

4. A process according to claim 3, in which zinc, silicon or sodium amalgam is used with a sodium or potassium hydroxide solution, at a reaction temperature of from 70°C to the boiling temperature of the reaction mixture.

5. A process according to claim 3, in which the rearrangement is carried out in hydrochloric acid of pH 1.5–0 at a temperature of from 10° to 50°C.

6. A process according to claim 3, in which, the compounds of formulae II and III, the ring A is substituted by only one sulphonic acid group.

7. A process according to claim 6, in which the resulting compound of formula I is of the formula Ia in which $R_1$, $R_2$ and $R_3$ each independently signifies
hydrogen, halogen or alkyl or alkoxy containing 1 to 6 carbon atoms.

8. A process according to claim 3, in which the substituents for rings A and B are selected from chlorine, methyl, methoxy, ethyl and ethoxy.

9. A process according to claim 1, in which simultaneous reduction and rearrangement is effected by treating the reaction product of the compounds of formulae II and III with tin chloride in a concentrated hydrochloric acid of pH 1.5–0 and at a temperature of from 0° to 30°C.

* * * * *